United States Patent
Suzuki

(10) Patent No.: US 8,974,492 B2
(45) Date of Patent: Mar. 10, 2015

(54) ENDOSCOPIC TREATMENT TOOL

(75) Inventor: Keita Suzuki, Tokyo (JP)

(73) Assignee: Olympus Medical Systems Corp. (JP)

( * ) Notice: Subject to any disclaimer, the term of this patent is extended or adjusted under 35 U.S.C. 154(b) by 0 days.

(21) Appl. No.: 12/884,680

(22) Filed: Sep. 17, 2010

(65) Prior Publication Data

US 2011/0071564 A1 Mar. 24, 2011

Related U.S. Application Data

(63) Continuation of application No. PCT/JP2009/070915, filed on Dec. 15, 2009.

(30) Foreign Application Priority Data

Mar. 18, 2009 (JP) ................................ 2009-066248

(51) Int. Cl.
  *A61B 17/00* (2006.01)
  *A61B 17/29* (2006.01)

(52) U.S. Cl.
  CPC ......... *A61B 17/29* (2013.01); *A61B 2017/2902* (2013.01); *A61B 2017/2905* (2013.01)
  USPC ............................ 606/205; 600/104; 600/106

(58) Field of Classification Search
  USPC ............................ 606/205–209; 600/104, 106
  See application file for complete search history.

(56) References Cited

U.S. PATENT DOCUMENTS

| | | | |
|---|---|---|---|
| 4,742,817 A * | 5/1988 | Kawashima et al. | 600/104 |
| 4,982,727 A * | 1/1991 | Sato | 600/104 |
| 5,271,543 A | 12/1993 | Grant et al. | |
| 5,501,694 A * | 3/1996 | Ressemann et al. | 606/159 |
| 5,746,696 A * | 5/1998 | Kondo | 600/139 |

(Continued)

FOREIGN PATENT DOCUMENTS

| | | |
|---|---|---|
| EP | 1 621 151 A2 | 2/2006 |
| JP | 2000-229084 | 8/2000 |

(Continued)

OTHER PUBLICATIONS

Search Report issued by European Patent Office on 09/2513 in connection with corresponding European Patent Application No. EP 09 841 916.1.

*Primary Examiner* — Katrina Stransky
(74) *Attorney, Agent, or Firm* — Ostrolenk Faber LLP

(57) ABSTRACT

An endoscopic treatment tool includes: a treatment part which is adapted to conduct treatment of tissue within a body cavity; an operation part which is adapted to operate the treatment part; an operation shaft member which connects the treatment part and the operation part; and a coil sheath part through which the operation shaft member passes so that the operation shaft member is capable of forward or backward movement, in which: the coil sheath part comprises: a first coil sheath around which wire is helically wound; and a second coil sheath that has a lower compressive resistance than the first coil sheath, and that has a higher rotation follow-up capability than the first coil sheath; the first coil sheath and the second coil sheath are disposed so as to coaxially and radially overlap; a first end part and a second end part of the second coil sheath are respectively connected to the treatment part and the operation part so as to be incapable of relative rotation around an axis of the second coil sheath; and at least one of the first end part and the second end part is capable of relative movement in an axial direction with respect to the first coil sheath.

8 Claims, 7 Drawing Sheets

(56) References Cited

U.S. PATENT DOCUMENTS

| | | | |
|---|---|---|---|
| 6,443,909 B1 * | 9/2002 | Ouchi | 600/562 |
| 6,461,310 B1 * | 10/2002 | Palmer et al. | 600/567 |
| 6,689,122 B2 * | 2/2004 | Yamamoto | 606/1 |
| 7,276,067 B2 * | 10/2007 | Bales et al. | 606/47 |
| 7,341,564 B2 * | 3/2008 | Zwiefel et al. | 600/564 |
| 2008/0194910 A1 | 8/2008 | Miyamoto et al. | 600/104 |
| 2008/0306334 A1 * | 12/2008 | Okada | 600/104 |

FOREIGN PATENT DOCUMENTS

| | | |
|---|---|---|
| JP | 2005-34623 | 2/2005 |
| JP | 2008-148738 | 7/2008 |
| JP | 2008-212620 | 9/2008 |
| JP | 2008-237266 | 10/2008 |

* cited by examiner

ENDOSCOPIC TREATMENT TOOL

BACKGROUND OF THE INVENTION

1. Field of the Invention

The present invention relates to an endoscopic treatment tool which is transendoscopically inserted into a body cavity and is employed in various procedures.

Priority is claimed on Japanese Patent Application No. 2009-066248, filed Mar. 18, 2009, the content of which is incorporated herein by reference.

2. Description of Related Art

Conventionally, endoscopic treatment tools provided with a treatment part such as forceps at the distal end have been known. When conducting treatment on tissue within a body cavity using such an endoscopic treatment tool, it may be necessary to adjust the orientation of a treatment part when the orientation of the treatment part that projects into the body cavity is inappropriate relative to the position of the tissue as a treatment target. When such adjustments are conducted, it is important to cause the treatment part to rotate in precise response to the operations of an operator.

Generally, when rotating a treatment part, an operation part at the proximal end side of the endoscopic treatment tool is rotated. In the case of a treatment tool such as forceps with which opening or closing operations are conducted by pushing or pulling an operating wire or the like that is connected to the treatment part via the operation part, compressive force is exerted in the axial direction of a coil sheath in conjunction with the opening or closing. At such times, compared to a single-strand coil sheath in which a single wire is wound, a multi-strand coil sheath in which multiple wires are wound has higher rotational transmittance, but tends to compress in the axial direction. Consequently, the coil sheath compresses in the axial direction, and the axial force to be transmitted to the distal part decreases, thereby making it impossible to conduct adequate treatment, and rendering procedures more complicated.

In order to solve this problem, the endoscopic treatment tool described in Japanese Unexamined Patent Application, First Publication No. 2008-212620 has been proposed. In this endoscopic treatment tool, a first coil sheath in which a single wire is helically wound is inserted through a second coil sheath in which multiple wires are helically wound in the same direction. The distal end of the second coil sheath is fixed to a movable distal part that serves to conduct treatment, while the proximal end thereof is fixed to an operation part.

In this manner, it is sought to combine compressive resistance and torque transmittance by employing the two types of coil sheath, namely, the first coil sheath and the second coil sheath.

SUMMARY OF THE INVENTION

An endoscopic treatment tool according to an aspect of the invention includes: a treatment part which is adapted to conduct treatment of tissue within a body cavity; an operation part which is adapted to operate the treatment part; an operation shaft member which connects the treatment part and the operation part; and a coil sheath part through which the operation shaft member passes so that the operation shaft member is capable of forward or backward movement, in which: the coil sheath part includes: a first coil sheath around which wire is helically wound; and a second coil sheath that has a lower compressive resistance than the first coil sheath, and that has a higher rotation follow-up capability than the first coil sheath; the first coil sheath and the second coil sheath are disposed so as to coaxially and radially overlap; a first end part and a second end part of the second coil sheath are respectively connected to the treatment part and the operation part so as to be incapable of relative rotation around an axis of the second coil sheath; and at least one of the first end part and the second end part is capable of relative movement in an axial direction with respect to the first coil sheath.

One of the first end part and the second end part of the second coil sheath may be capable of relative movement in the axial direction with respect to the first coil sheath, and the other one of the first end part and the second end part may be incapable of relative movement in the axial direction with respect to the first coil sheath.

The first coil sheath may be formed by helically winding a single wire; and the second coil sheath may be formed by helically winding multiple wires in the same direction.

A first end part and a second end part of the first coil sheath may be respectively connected to the treatment part and the operation part so as to be capable of relative rotation around an axis of the first coil sheath and incapable of relative movement in the axial direction.

The treatment part may have a pair of forcep members that can be opened and closed.

DETAILED DESCRIPTION OF THE INVENTION

Figure 1:
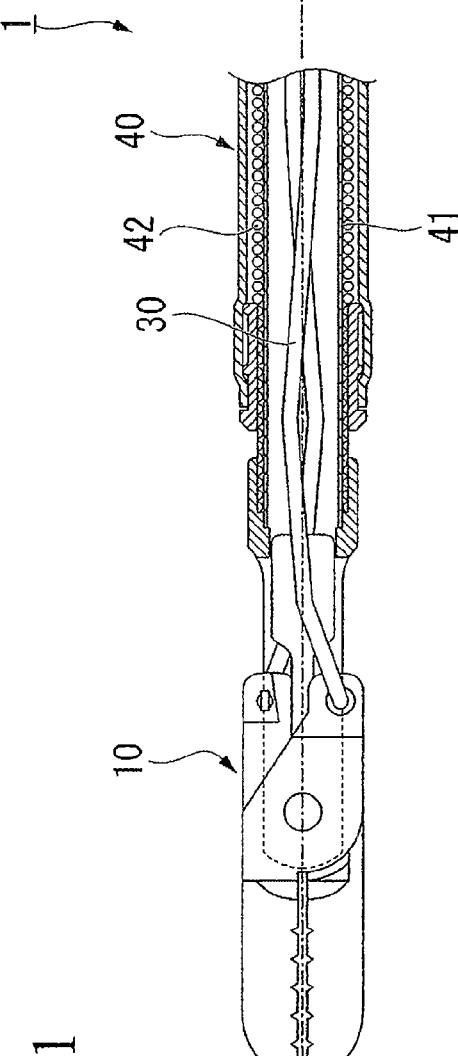
FIG. 1 is an overall view of an endoscopic treatment tool of a first embodiment of the present invention.
Figure 1:
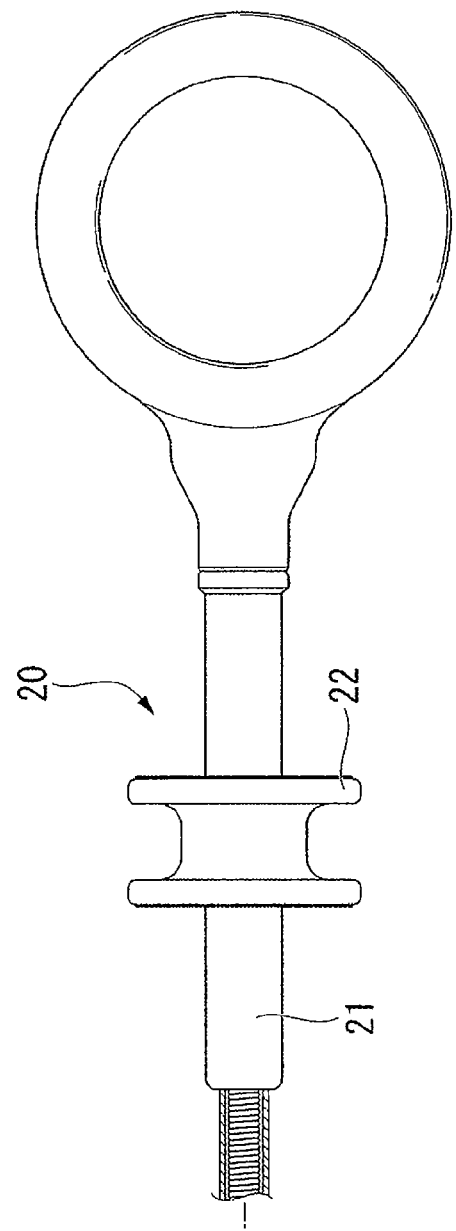

Below, an endoscopic treatment tool of a first embodiment of the present invention is described with reference to FIG. 1 to FIG. 6. As shown in FIG. 1, an endoscopic treatment tool (hereinafter simply "treatment tool") 1 of the present embodiment is provided with a treatment part 10 for conducting treatment of tissue within a body cavity, an operation part 20 for operating the treatment part 10, two operating wires (operation shaft members) 30 which connects the treatment part 10 and the operation part 20, and a coil sheath part 40 through which the operating wires 30 pass so as to be capable of forward and backward movement.

Figure 2:
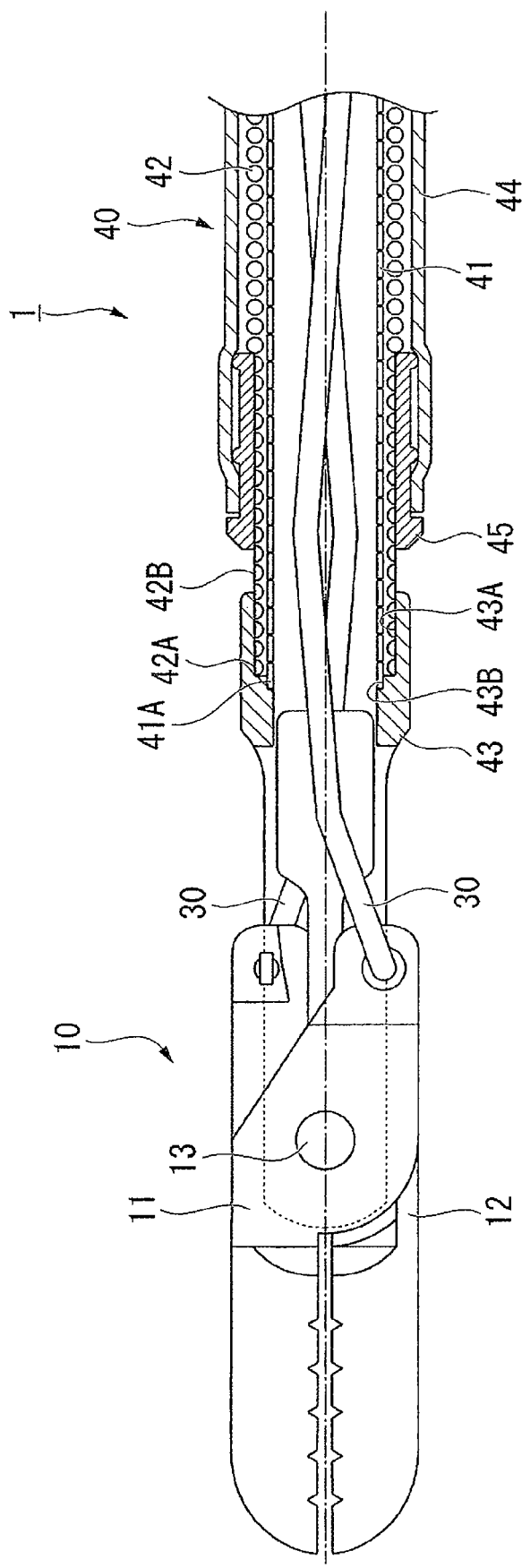
FIG. 2 is an enlarged sectional view of a distal end part of the same endoscopic treatment tool.

FIG. 2 is an enlarged sectional view of the distal portion of the treatment tool 1 including the treatment part 10. The treatment part 10 is configured by connecting a pair of forcep members—a first forcep member 11 and a second forcep member 12—with a pivot shaft 13 so as to be capable of mutually and freely turning. The operating wires 30 are connected to the proximal end parts of the respective forcep members 11 and 12, more toward the proximal side than the pivot shaft 13, pass through the interior of the coil sheath part 40, and are connected to the operation part 20.

As shown in FIG. 1, the operation part 20 is configured by providing a long and slender main body 21, and a slider 22 that is attached so as to be capable of sliding within a fixed range in the axial direction with respect to the main body 21. The end parts of the operating wires 30 and the coil sheath part 40 are connected to the operation part 20; the detailed connection mode is described below.

The coil sheath part 40 is to be transendoscopically inserted into a body cavity, and is provided with a first coil sheath 41 through which the operating wires 30 pass, and a second coil sheath 42 through which the first coil sheath 41 passes.

The first coil sheath 41 is a so-called single-strand type coil sheath that is formed by tightly winding a single metal wire in a loop shape. The first coil sheath 41 imparts compressive resistance to the inserted operating wires 30, and appropriately transmits the opening and closing operation of the treatment part 10 to the treatment part 10 via the slider 22.

On the other hand, the second coil sheath 42 is a so-called multi-strand type coil sheath that is formed by tightly winding multiple metal wires side-by-side in the radial direction in a loop shape. The second coil sheath 42 appropriately transmits the operations that serve to rotate the treatment part 10 to the treatment part 10. The number of metal wires that are used to form the second coil sheath 42 may be decided at one's discretion.

In the present embodiment, the case is described where the first coil sheath 41 is formed with a planar metal wire, while the second coil sheath 42 is formed with round rod-like metal wires, but the metal wire shapes are not limited thereto, and may be appropriately selected according to design values and the like of the coil sheath part 40.

As shown in FIG. 2, a region of prescribed length at a distal end (first end part) 42A side of the second coil sheath 42 is worked by machining or the like so as to have a planar outer circumferential surface 42B. A connecting member 43 that serves to connect the treatment part 10 and the coil sheath part 40 is fixed to the distal end 42A of the second coil sheath 42 by welding or the like. The pivot shaft 13 is provided at more toward the distal end side than the connecting member 43, and the pivot shaft 13 is incapable of relative movement with respect to the connecting member 43.

The proximal end part of the connecting member 43 is formed in a tubular shape, and its inner surface is provided with a first inner surface 43A that is connected and fixed to the outer circumferential surface of the second coil sheath 42, and a second inner surface 43B that is formed with a smaller diameter than the first inner surface 43A more toward the distal end side than the first inner surface 43A. A distal end 41A of the first coil sheath 41 that passes through the second coil sheath 42 is inserted into the second inner surface 43B, and is fixed to the connecting member 43.

That is, the distal end 42A of the second coil sheath 42 that is fixed to the first inner surface 43A of the connecting member 43 is incapable of rotating around its own axis with respect to the connecting member 43, and is incapable of relative movement in the axial direction with respect to the first coil sheath 41.

The connection mode of the connecting member 43 and the coil sheath part is not specifically limited to that described above. For example, it is acceptable to adopt a configuration where the second coil sheath 42 is fixed to an outer surface of a proximal end part of a connecting member that is formed in a tubular shape, and the first coil sheath 41 is fixed to an inner surface of the proximal end part of the connecting member. Moreover, the shape of the site in the connecting member where the coil sheath part is fixed does not have to be tubular.

The outer circumferential surface of the second coil sheath 42 is covered by an insulating tube 44. The tube 44 is formed with an insulating material, and an engagement member 45 of approximately cylindrical shape is attached to its distal end part by press fitting or the like. The engagement member 45 engages with the distal end part of the outer circumferential surface 42B whose outer diameter is diminished by the aforementioned work.

By adopting such a configuration, the tube 44 is attached so that it is capable of relative rotation around an axis with respect to the second coil sheath 42. The tube 44 is not indispensable to the treatment tool of the present invention, and may be provided as necessary in cases where insulating treatment of the coil sheath part 40 is required. Accordingly, it is also acceptable to configure the treatment tool 1 so that the outer circumferential surface of the second coil sheath 42 is uncovered and exposed.

Figure 3:
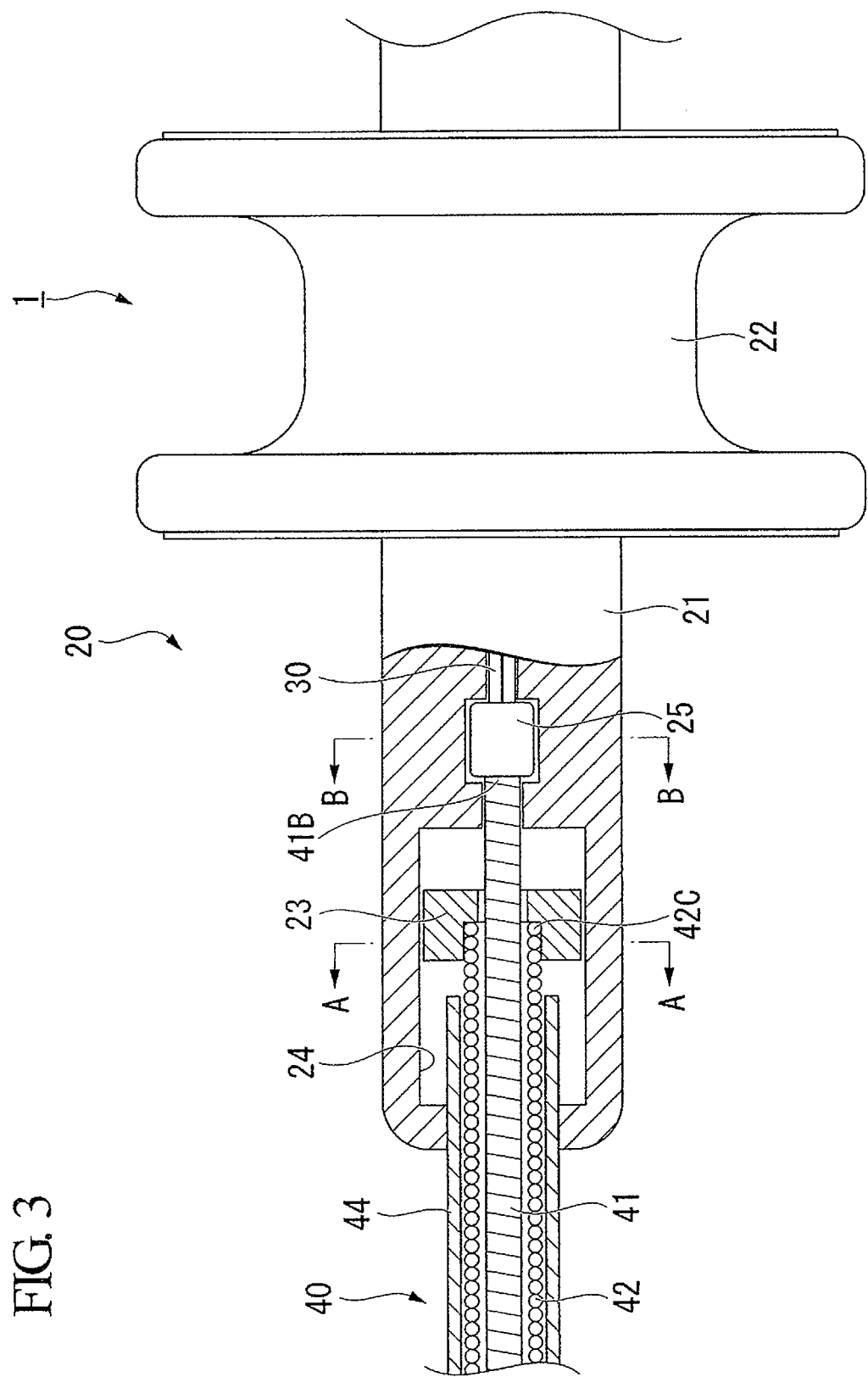
FIG. 3 is an enlarged sectional view of an operation part of the same endoscopic treatment tool.

FIG. 3 is an enlarged sectional view of the connection site of the operation part 20 and the coil sheath part 40. The proximal end part of the coil sheath part 40 is connected to the main body 21. The proximal end part of the tube 44 is inserted into the distal end part of the main body 21 so as to be capable of relative rotation, and the proximal end (second end part) 42C of the second coil sheath 42 is fixed to the sliding member 23 inside the main body 21.

Figure 4:
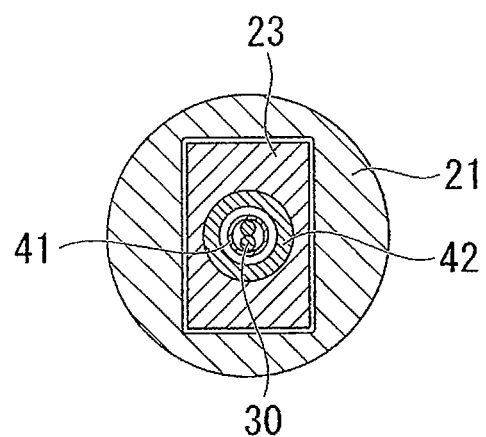
FIG. 4 is a sectional view along line A-A of FIG. 3.

FIG. 4 is a sectional view along the A-A line of FIG. 3. As shown in FIG. 4, since the sectional shape of the sliding member 23 is approximately rectangular in the widthwise direction of the main body 21, when the main body 21 is axially rotated, the sliding member 23 and the second coil sheath 42 also axially rotate in conjunction with the main body 21.

Moreover, the sliding member 23 is capable of sliding inside a slide groove 24 that is provided inside the main body 21 so as to extend lengthwise. That is, the proximal end 42C of the second coil sheath 42 is attached so as to be incapable of axially turning with respect to the main body 21, and capable of relative movement in the axial direction with respect to the main body 21 and the first coil sheath 41. It is preferable to set the positional relation of the sliding member 23 in the slide groove 24 so that the sliding member 23 never makes contact with the lengthwise end faces of the slide groove 24 in order that strain does not occur in the coil sheath part 40 even when the coil sheath part 40 is maximally flexed.

Figure 5:
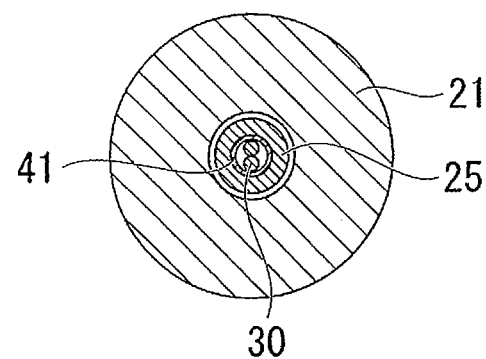
FIG. 5 is a sectional view along line B-B of FIG. 3.

The proximal end 41B of the first coil sheath 41 which extends from the second coil sheath 42 is fixed to an engagement member 25. As shown in FIG. 5, the engagement member 25 is approximately cylindrical in shape, and has a larger outer diameter than the first coil sheath 41. Accordingly, the proximal end 41B of the first coil sheath 41 is attached so as to be capable of axial rotation and incapable of relative movement in the axial direction with respect to the main body 21. The operating wires 30 which extend from the first coil sheath 41 pass through the interior of the main body 21, and are connected to the slider 22. Consequently, by sliding the slider 22 in the axial direction relative to the main body 21, it is possible to move the operating wires 30 forward or backward relative to the coil sheath part 40, and conduct opening or closing operation of the pair of forcep members 11 and 12 that are provided in the treatment part 10.

Operations during use of the treatment tool 1 that is configured in the foregoing manner are now described.

First, the user inserts an endoscope (not illustrated in the drawings) into the body of a patient or the like, and advances the distal end of the endoscope to the vicinity of tissue as a treatment target within a body cavity (hereinafter referred to as "target tissue").

Next, the user moves the slider 22 backward relative to the main body 21 to put the treatment part 10 into a closed condition, and inserts the treatment part 10 and the coil sheath part 40 of the treatment tool 1 into the forceps channel (not illustrated in the drawings) of the endoscope. The user then projects the treatment part 10 from forceps channel.

When treatment is conducted, the slider 22 is slid toward the distal end of the main body 21, whereupon the operating wires 30 which are connected to the slider 22 move forward relative to the coil sheath part 40. As stated above, the pivot shaft 13 is incapable of relative movement with respect to the connecting member 43 that is attached to the distal end of the coil sheath part 40, with the result that the first forcep member 11 and second forcep member 12 are respectively turned centering on the pivot shaft 13, and the treatment part 10 is opened.

When the user has positioned the target tissue between the open forcep members 11 and 12 of the treatment part 10, and slides the slider 22 toward the proximal end of the main body 21, the distal end parts of the forcep members 11 and 12 close again, and the target tissue is sandwiched by the treatment part 10. At this time, as compressive resistance is imparted to the operating wires 30 by the single-strand type first coil sheath 41, the operation by the user is satisfactorily transmitted to the treatment part 10 via the slider 22.

In the case where the opening/closing orientation of the forcep members 11 and 12 of the treatment part 10 that extends from the distal end of the endoscope is inappropriate with respect to the target tissue, the user grasps the main body 21 of the operation part 20, and rotates it around the axis, whereupon the sliding member 23 is axially rotated in conjunction with the main body 21, as are the second coil sheath 42 that is connected to the sliding member 23 and the treatment part 10 that is attached to the distal end of the second coil sheath 42. In this manner, it is possible to adjust the opening/closing orientation of the treatment part 10. Since the treatment part 10 and the main body 21 of the operation part 20 are connected by the multi-strand type second coil sheath 42, the torque generated by the above-described rotational operation of the main body 21 by the user is satisfactorily transmitted to the treatment part 10 by the second coil sheath 42. As a result, the treatment part 10 axially rotates while satisfactorily following the rotational operation of the main body 21, thereby enabling adjustment of the opening/closing orientation of the treatment part 10 to be easily conducted.

Figure 6:
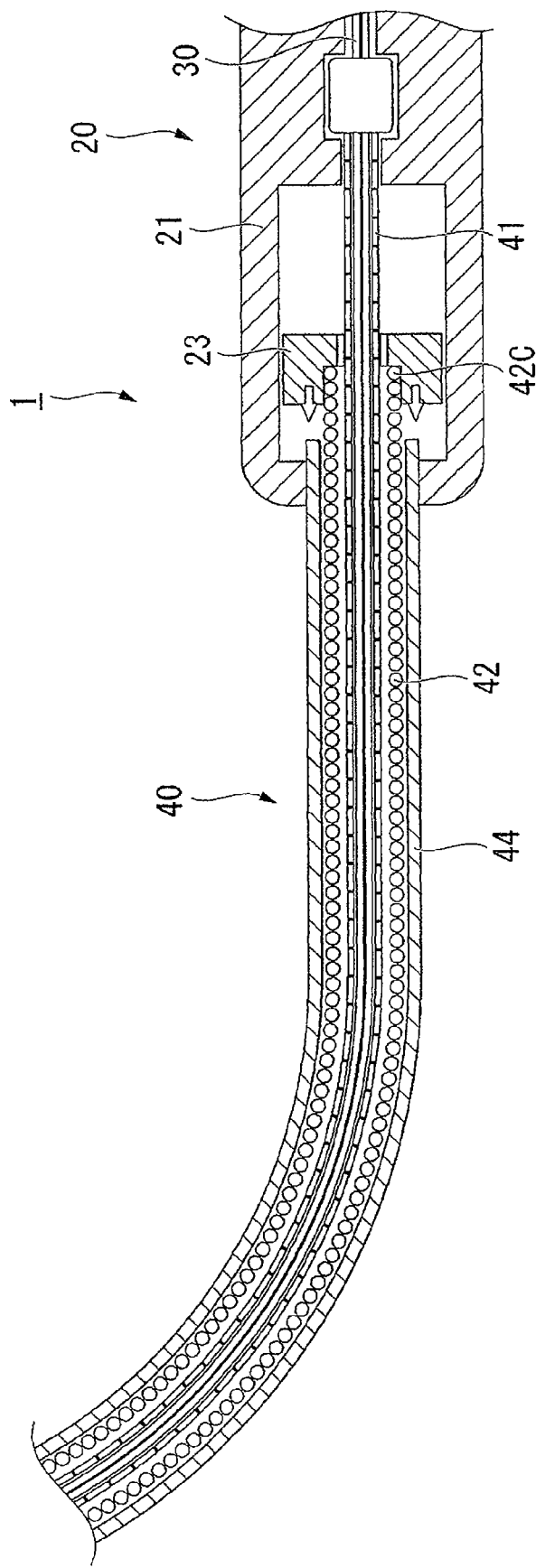
FIG. 6 is a drawing that shows operations during use of the same endoscopic treatment tool.

Depending on the form of the organ or the like within the body cavity and the posture of the patient, meandering, flexing or the like may occur in the long inserted portion of the endoscope and in the coil sheath part 40 of the treatment tool 1 that passes through the inserted portion. However, as shown in FIG. 6, even in the case where a difference in apparent length occurs between the first coil sheath 41 and the second coil sheath 42 that configure the coil sheath part 40 due to meandering or the like of the coil sheath part 40, the sliding member 23 to which the proximal end 42C of the second coil sheath 42 is connected slides in the direction shown by the arrow within the slide groove 24 inside the main body 21, with the result that the proximal end 42C of the second coil sheath 42 undergoes relative movement in the axial direction with respect to the first coil sheath 41, absorbing the apparent length. In this manner, the accumulation of strain in the coil sheath part 40 accompanying rotational operation is inhibited.

It should be noted that FIG. 6 is shown with omission of the tube 44 in order to facilitate viewing of the drawing.

According to the treatment tool 1 of the present embodiment, the two ends of the multi-strand type second coil sheath 42 are respectively attached to the treatment part 10 and the main body 21 of the operation part 20 so as to be incapable of turning. Accordingly, the torque generated by the axial rotation of the main body 21 is efficiently transmitted to the treatment part 10, causing axial rotation of the treatment part 10, and enabling adjustment of orientation relative to the target tissue to be satisfactorily conducted.

Moreover, since the proximal end 42C of the second coil sheath 42 is capable of relative movement in the axial direction with respect to the first coil sheath 41 by the sliding member 23 and the slide groove 24 provided in the main body 21, even in the case where the coil sheath part 40 meanders within the body cavity, accumulation of strain in the coil sheath part 40 is inhibited. Consequently, it is possible to satisfactorily prevent rotational skipping when the treatment part 10 is axially rotated.

In the present embodiment, the case was described where the single-strand type first coil sheath 41 is inserted through the multi-strand type second coil sheath 42, but so long as the first coil sheath 41 and the second coil sheath 42 are arranged so as to overlap approximately coaxially in the radial direction as in the above-described case, the positional relation of the two is not limited thereto.

Figure 7:
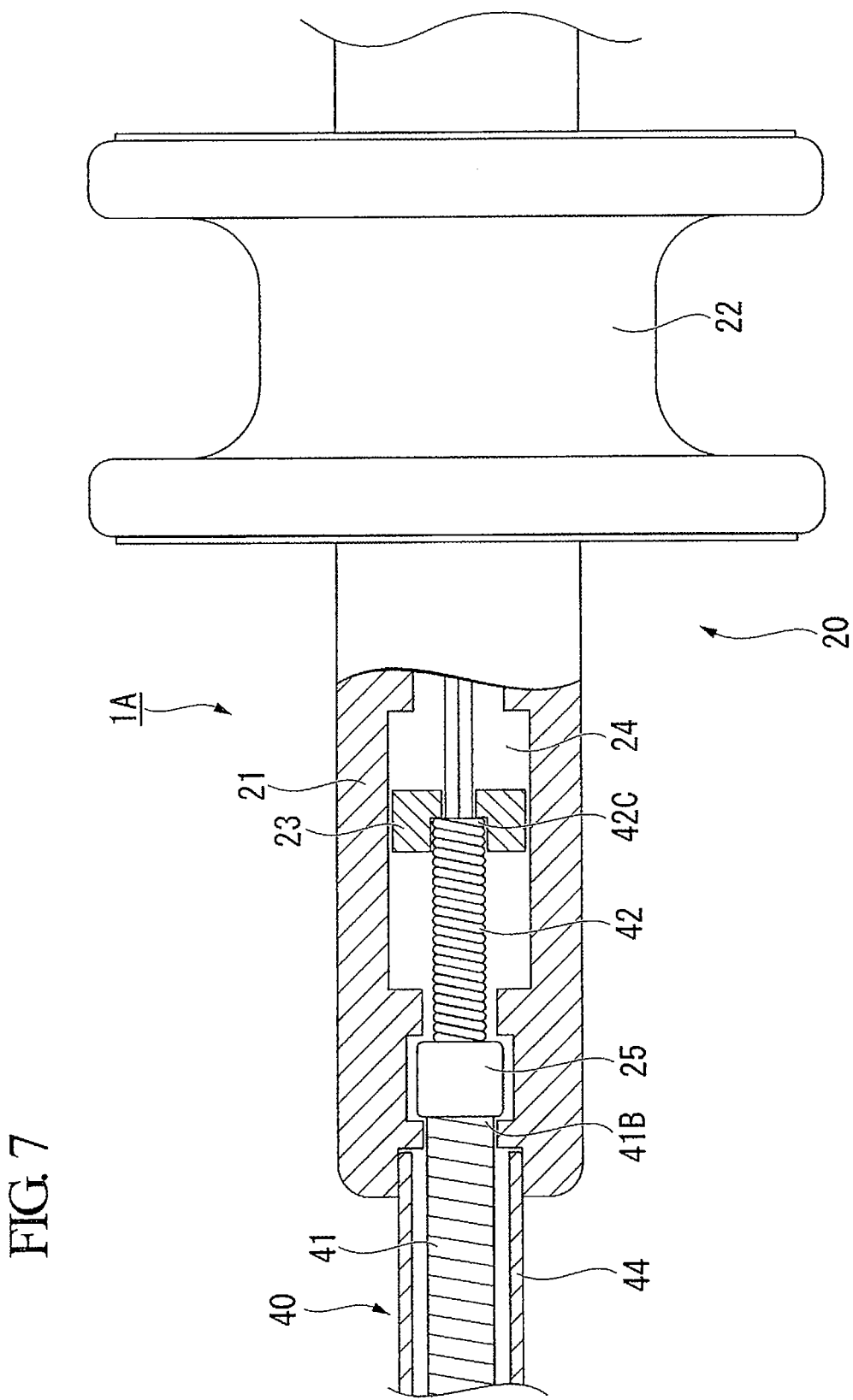
FIG. 7 is an enlarged sectional view of an operation part of an endoscopic treatment tool of a modified example of the first embodiment.

For example, as with a treatment tool 1A of a modified example shown in FIG. 7, it is also acceptable to configure the coil sheath part 40 so that the second coil sheath 42 is inserted through the first coil sheath 41. In the modified example shown in FIG. 7, the proximal end 41B of the first coil sheath 41 is attached to the main body 21 by the engagement member 25 more toward the distal end side than the slide groove 24, and the sliding member 23 is attached to the proximal end 42C of the second coil sheath 42 that extends from the proximal end 41B of the first coil sheath 41 and is disposed in the slide groove 24. Even in this case, it is possible to obtain the same effect as the treatment tool 1 described above.

Moreover, it is also acceptable to attach the distal end 41A of the first coil sheath 41 so that it is capable of relative axial rotation with respect to the distal end member. When configured in this manner, the first coil sheath 41 is also capable of relative axial rotation with respect to the second coil sheath 42. Accordingly, it is possible to configure a treatment tool that has good operational feel in which rotation of the second coil sheath 42 becomes smoother when the treatment part 10 is rotationally operated.

Next, a second embodiment of the present invention is described with reference to FIG. 8. The difference between a treatment tool 51 of the present embodiment and the treatment tool 1 is the mode of connection of the coil sheath part to the treatment part and the operation part.

It should be noted that elements of configuration that are common to the treatment tool 1 of the first embodiment are given the same reference numerals, and duplicative description thereof is omitted.

Figure 8:
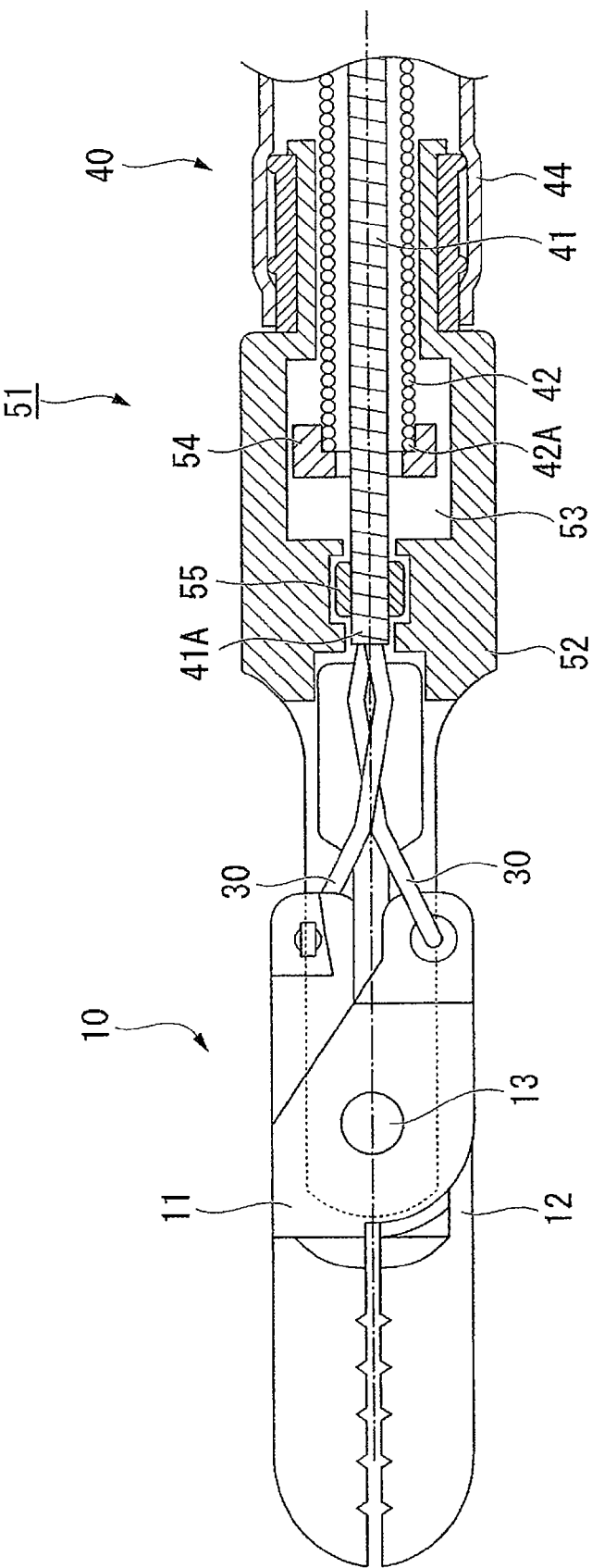
FIG. 8 is a partially enlarged sectional view of an endoscopic treatment tool of a second embodiment of the present invention.

FIG. 8 is an enlarged sectional view of the vicinity of the distal end of the coil sheath part 40 of the treatment tool 51. In the treatment tool 51, the treatment part 10 and the coil sheath 40 are connected by a connecting member 52.

The connecting member 52 has longer axial dimensions than the connecting member 43 of the first embodiment, and is attached so as to be capable of relative rotation around its own axis with respect to the tube 44.

A slide groove 53 having the same configuration as the slide groove 24 of the first embodiment is provided inside the connecting member 52, and a sliding member 54 is attached to the distal end 42A of the second coil sheath 42 and is disposed within the slide groove 53. An engagement member 55 having the same configuration as the engagement member 25 of the first embodiment is attached to the distal end 41A of the first coil sheath 41 that extends from the distal end 42A of the second coil sheath 42, and the first coil sheath 41 is attached to the connecting member 52 in approximately the same mode as the connection of the first coil sheath 41 and the main body 21 in the first embodiment.

With this configuration, the distal end 41A of the first coil sheath 41 is attached so that it is capable of relative rotation around its own axis and incapable of relative movement in the axial direction with respect to the connecting member 52 in the treatment part 10 side. Further, the distal end 42A of the second coil sheath 42 is attached so that it is incapable of relative rotation around its own axis and capable of relative movement in the axial direction with respect to the connecting member 52. As a result, the distal end 42A of the second coil sheath 42 is configured so that it is capable of axial rotation and capable of relative movement in the axial direction with respect to the first coil sheath 41.

The proximal end 42C of the second coil sheath 42 is not illustrated in the drawings, but is connected so that it is incapable of axial rotation and incapable of relative movement in the axial direction with respect to the operation part 20, in a manner that is approximately identical to the mode of connection of the distal end 42A to the connecting member 43 in the treatment tool 1.

With the treatment tool 51 of the present embodiment that is configured as described above, when the coil sheath part 40 flexes due to meandering or the like, the distal end 42A of the second coil sheath 42 undergoes relative movement in the axial direction with respect to the first coil sheath 41 by moving toward the proximal end within the slide groove 53. As a result, the difference in the apparent length of the first coil sheath 41 and the second coil sheath 42 is absorbed, and accumulation of strain in the coil sheath part 40 is inhibited. Accordingly, as with the treatment tool 1 of the first embodiment, it is possible to satisfactorily conduct rotational operation of the treatment part 10 while suppressing rotational skipping.

While preferred embodiments of the invention have been described and illustrated above, the invention is not to be considered as being limited by the above embodiments and various modifications can be made without departing from the scope of the present invention.

For example, in each of the embodiments described above, the case was described where the first coil sheath is a single-strand type coil sheath, and the second coil sheath is a multi-strand type coil sheath, but the combination of coil sheaths is not limited thereto. As one example, one may cite the case where the first coil sheath is a two-strand type coil sheath composed of two wires, and the second coil sheath is a five-strand type coil sheath composed of five wires. In this case, both the first coil sheath and the second coil sheath are multi-strand type coil sheaths, and in this case as well, it is possible to obtain the same effects, because the first coil sheath has a higher compressive resistance than the second coil sheath, and the second coil sheath has a higher rotation follow-on capability than the first coil sheath.

However, in order to obtain sufficient compressive resistance, it is preferable to use a first coil sheath composed of three wires or less.

Moreover, in each of the embodiments described above, the case was described where only one of either the proximal end part and the distal end part of the second coil sheath was capable of relative movement in the axial direction with respect to the first coil sheath, but as it is possible to obtain the effects of the present invention so long as at least one of the end parts of the second coil sheath is capable of relative movement in the axial direction with respect to the first coil sheath, it is also acceptable to adopt a configuration where both the proximal end part and distal end part are capable of relative movement in the axial direction with respect to the first coil sheath.

Furthermore, in each of the embodiments described above, the case was described where operating wires are used as the operation shaft members, but instead of this, it is also acceptable to configure the operation shaft members using rods or pipes, or a combination of these.

In addition, in each of the embodiments described above, the case was described where the treatment part is composed of a pair of forcep members, but the treatment part in the treatment tool of the present invention is not limited thereto. That is, so long as it is a treatment part that requires adjustment of orientation relative to tissue as treatment target, it is possible to apply treatment parts of any type such as, for example, a snare wire or a so-called two-legged forceps.

According to the endoscopic treatment tool of the present invention, it is possible to cause a treatment part to rotate by satisfactorily following rotational operation of an operation part, even when it is in a flexed state.

According to the endoscopic treatment tool of the present invention, when the coil sheath part experiences meandering or the like within a body, and a difference in apparent length occurs between the first coil sheath and the second coil sheath, the difference in apparent length is absorbed by the movement of one of the end parts of the second coil sheath that is capable of relative movement with respect to the first coil sheath, and the accumulation of stress in the coil sheath part is inhibited at the time of rotational operation of the second coil sheath.

The first coil sheath may be formed by helically winding a single wire, and the second coil sheath may be formed by helically winding multiple wires in the same direction. In this case, it is possible to optimize the compressive resistance of the first coil sheath and the rotation follow-up capability of the second coil sheath.

The first end part and the second end part of the first coil sheath may be respectively connected to the treatment part and the operation part so as to be capable of relative rotation around an axis of the first coil sheath and incapable of relative movement in the axial direction. In this case, it is possible to enable appropriate rotational operation of the treatment part while reliably providing compressive resistance to the operation shaft member.

What is claimed is:
1. An endoscopic treatment tool, comprising:
   a treatment part which is adapted to conduct treatment of tissue within a body cavity;
   an operation part which is adapted to operate the treatment part, the operation part includes a main body in which a sliding space elongated in a longitudinal direction inside the main body is formed and a slider slidingly coupled to the main body and configured to be capable of relatively sliding with respect to the main body;
   an operation shaft member which connects the treatment part and the slider, the operation shaft member which is capable of moving relative to the main body in an axial direction of the operation shaft member; and
   a coil sheath part through which the operation shaft member passes so that the operation shaft member is capable of forward or backward movement, wherein the coil sheath part further comprises:
      a first coil sheath around which a wire is helically wound; and a second coil sheath that has a lower compressive resistance than the first coil sheath and has a higher rotation follow-up capability than the first coil sheath, the first coil sheath and the second coil sheath are disposed so as to coaxially and radially overlap, a first end part of the second coil sheath is connected to the treatment part so as to be incapable of rotating around an axis of the second coil sheath relative to the treatment part, a second end part of the second coil sheath is connected to a sliding member which is configured to freely slide inside the sliding space along the axis of the second coil sheath, the second end part of the second coil sheath and the sliding member are inserted into the sliding space and freely slide inside the sliding space in an axial direction of the first coil sheath, the second end part of the second coil sheath and the sliding member are configured to be incapable of rotating around the axis of the second coil sheath relative to the main body, a first end part and a second end part of the first coil sheath are respectively connected to the treatment part and the main body so as to be incapable of moving relative to the treatment part and the main body in the axial direction of the first coil sheath, the operation part, the second coil sheath and the treatment part relatively rotate with respect to the first coil sheath, and the sliding member slides inside the sliding space in the axial direction of the second coil sheath in accordance with a difference in length between the first coil sheath and the second coil sheath occurring during bending of the coil sheath part.

2. The endoscopic treatment tool according to claim 1, wherein one of the first end part and the second end part of the second coil sheath is capable of relative movement in the axial direction with respect to the first coil sheath, and the other one of the first end part and the second end part is incapable of relative movement in the axial direction with respect to the first coil sheath.

3. The endoscopic treatment tool according to claim 1, wherein:
the first coil sheath is formed by helically winding a single wire; and
the second coil sheath is formed by helically winding multiple wires in the same direction.

4. The endoscopic treatment tool according to claim 1, wherein the first end part and the second end part of the first coil sheath are respectively connected to the treatment part and the operation part so as to be capable of relative rotation around an axis of the first coil sheath and incapable of relative movement in the axial direction.

5. The endoscopic treatment tool according to claim 1, wherein the treatment part has a pair of forcep members that can be opened and closed.

6. The endoscopic treatment tool according to claim 1, wherein at least one end of the first coil sheath extends from one end of the second coil sheath in a direction of the axis of the first coil sheath and the second coil sheath.

7. The endoscopic treatment tool according to claim 1, wherein
the second end part of the second coil sheath is configured to be prevented from axially turning with respect to the main body and to be capable of relative movement in the axial direction with respect to the main body and the first coil sheath, and
the second end of the first coil sheath is configured to be prevented from relative movement in the axial direction with respect to the main body.

8. The endoscopic treatment tool according to claim 1, wherein the second end part of the first coil sheath is inserted into the sliding space and is connected to the main body.

* * * * *